United States Patent [19]

Esper

[11] Patent Number: 4,766,903
[45] Date of Patent: Aug. 30, 1988

[54] APPARATUS FOR DETECTING OF VOLTAGES OR CHARGES ON THE HUMAN BODY AND FOR REMOVING SUCH STRESSES OR CHARGES FROM THE HUMAN BODY

[76] Inventor: Herbert Esper, Bgm-Heinrich -Strasse 23, 8403 Bad Abbach, Fed. Rep. of Germany

[21] Appl. No.: 572,183

[22] Filed: Jan. 19, 1984

[30] Foreign Application Priority Data

Jul. 8, 1983 [EP] European Pat. Off. ........ 83106720.2

[51] Int. Cl.⁴ ............................ A61B 5/00; H05F 3/00
[52] U.S. Cl. .................................... 128/630; 128/908; 361/232
[58] Field of Search ........................ 128/908, 734–735, 128/630; 361/212, 232

[56] References Cited

U.S. PATENT DOCUMENTS

| 3,211,153 | 10/1965 | Gambetti | 361/232 X |
| 3,603,811 | 9/1971 | Day et al. | 128/908 X |
| 3,656,025 | 4/1972 | Roveti | 128/908 X |
| 3,968,802 | 7/1976 | Ballis | 128/908 X |
| 4,523,252 | 6/1985 | Wallen | 361/212 |

FOREIGN PATENT DOCUMENTS 0612331  5/1978  U.S.S.R. .............. 128/908

Primary Examiner—Edward M. Coven
Assistant Examiner—Angela D. Sykes
Attorney, Agent, or Firm—Jacobs & Jacobs

[57] ABSTRACT

Apparatus for partial detection of voltages or charges on the body of a human or animal and for the removal of such voltages or charges, which comprises at least one element which acts as an amplifier or as an electrically controllable switch and has a working-current circuit and a control-current circuit, the latter having a control connection and a common connection for the control-current circuit and working-current circuit; an electrode acting as a probe which is connected to the control connection; an indicating device which is controlled by the current in the working-current circuit; and a voltage control element which, in the absence of external voltage on the probe, maintains the control connection at a predetermined voltage level.

12 Claims, 1 Drawing Sheet

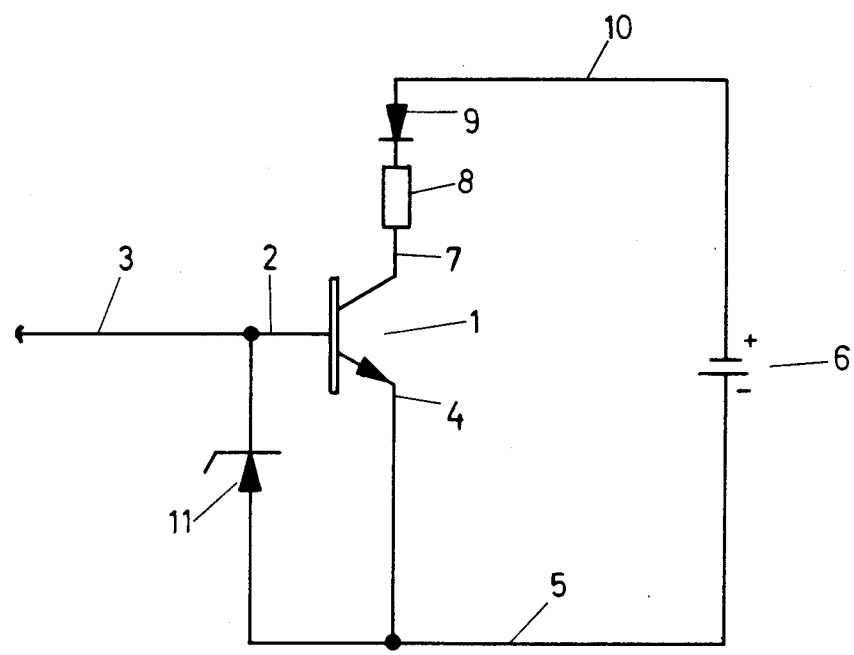

APPARATUS FOR DETECTING OF VOLTAGES OR CHARGES ON THE HUMAN BODY AND FOR REMOVING SUCH STRESSES OR CHARGES FROM THE HUMAN BODY

It is generally recognized today that voltages or concentrations of charge carriers may occur on the surface of the skin of persons in various regions of the body, it not only being necessary to remove these partial voltages or charge-carrier concentrations in order to avoid impairment of health but it being also possible to draw conclusions as to diseased or susceptible parts or organs of the body from these partial voltages or charge-carrier concentrations as a function of the parts of the body on which these voltages or charge-carrier concentrations occur.

The object of the invention is to provide an apparatus by means of which it is possible to remove partial voltages or charges from the human body, the apparatus affording the possibility of indicating this discharge process, and thus also the complete removal of voltages or charges, and of determining those regions of the body on which partial voltages or charge-carrier concentrations are present in order in this way to be able to draw conclusions as to diseased or susceptible parts or organs of the body.

In order to achieve this purpose, an apparatus of the type described above is characterized, according to the invention, by at least one element which acts as amplifier or electrically controllable switch and has a working-current circuit and a control-current circuit, the latter having a control connection as well as a common connection for the control-current circuit and the working-current circuit; by an electrode serving as probe which is connected to the control connection; by an indicating device controlled by the current in the working-current circuit; and by means which, in the absence of external voltage on the probe maintain the control connection at a predetermined voltage level.

In a preferred embodiment of the apparatus of the invention, said last-mentioned means are developed in such a manner that, in the absence of external voltage on the probe, they maintain the control connection of the element acting as amplifier or an electronically controllable switch at a voltage level which does not permit any current in the working-current circuit or else only a current of such size in said working-current circuit that the indicating device does not produce any indication. The means which determine the voltage level of the control connection in the absence of external voltage on the probe or the bias voltage of the control connection are then formed in the simplest case, for instance, by a high-ohmic resistor or a zener diode which lies in the control current circuit preferably parallel to the control connection and to the common connection for the control current circuit and the working current circuit.

In one particularly simple embodiment of the apparatus of the invention, the element which acts as amplifier or electronically controllable switch is at least one transistor whose base then forms the control connection and whose emitter forms the common connection for the control-circuit current and working-circuit current.

The indicating device is then preferably located in the collector current circuit of this transistor or else in the collector or emitter current circuit of another subsequent transistor or else in the output circuit of an amplifier element which is arranged behind the first transistor.

The indicating device preferably consists of a light-emitting diode.

BRIEF DESCRIPTION OF THE DRAWING

The invention will be described below with reference to the drawing which shows one illustrative embodiment.

DESCRIPTION OF THE PREFERRED EMBODIMENT

In the drawing, 1 is a transistor of npn-type. The base 2 of this transistor is connected directly to the one end of an electrode 3 which serves as probe the other, free end of which can be brought into contact with the surface of the skin of a human body in order to detect and remove voltages or charge carriers. The probe 3 consists, of course, of electrically conductive material, at least the surface of this probe being formed of a corrosion-resistant material (for instance silver). The emitter 4 of the transistor 1 is connected via a wire 5 to the negative terminal of a battery 6. The collector 7 is connected, via the series connection of a protective resistor 8 and a light-emitting diode 9 serving as indicating device, by means of the wire 10 to the positive terminal of the battery 6.

Parallel to the base-emitter path of the transistor 1 there is a zener diode 11 which forms a very high-ohmic base leak resistor.

If now, by scanning the surface of the skin of the human body, voltages which are positive as compared with the emitter are found at a given place, then the normally closed transistor 1 is opened, as a result of which a current flows in the collector-emitter circuit through the light-emitting diode 9 and causes the latter to light up until the voltages have been completely removed at the point of the body in question, primarily via the base-emitter path of the transistor 1. After the reduction or removal of these voltages, the transistor 1 is again brought into its blocking position and extinguishes the light-emitting diode.

The invention has been described above with reference to an illustrative embodiment. It is obvious that changes and modifications are possible without thereby going beyond the inventive concept which forms the basis of the invention. Thus it is possible, for instance, to replace the zener diode 11 by a high-ohmic resistor, although a zener diode is more advantageous in view of its better reproducibility.

Furthermore, it is, of course, also possible to use, instead of an npn transistor, a transistor 1 of nnp type, subject to suitable reversal of the connections of the battery 6, the light-emitting diode 9 and the zener diode 11, in which case negative voltages on the electrode 1 cause a response of the light-emitting diode.

Finally, it is also possible to use, instead of the transistor 1 shown in the drawing, a field-effect transistor, which is characterized by a particularly high input resistance.

I claim:

1. Apparatus for detecting voltages or charges on the body of a human or animal, which comprises an electrical conductive probe; a controllable electrical circuit comprising a control-current loop and a working current loop, said control-current loop and said working current loop having a common electrical connection; said control-current loop having a control connection electrically connected to said probe and having voltage maintaining means for maintaining said control connection at a predetermined voltage level in the absence of external voltage on said probe; and said working current loop including an indicator means for indicating flow of current in said working current loop.

2. Apparatus according to claim 1, wherein said controllable electrical circuit is an amplifier.

3. Apparatus according to claim 1, wherein said controllable electrical circuit is an electrically controllable switch.

4. Apparatus according to claim 1, wherein said is a transistor.

5. Apparatus according to claim 4 wherein said control connection is formed by the base of said transistor.

6. Apparatus according to claim 5, wherein said common connection is formed by the emitter of said transistor.

7. Apparatus according to claim 1, wherein said voltage maintaining means comprises at least one diode.

8. Apparatus according to claim 1, wherein said voltage maintaining means comprises at least one zener diode.

9. Apparatus according to claim 1, wherein said voltage maintaining means comprises at least one resistor.

10. Apparatus according to claim 1, wherein said voltage maintaining means is parallel to the control connection and common connection.

11. Apparatus according to claim 1, wherein said indicator is a light-emitting diode.

12. Apparatus according to claim 11, wherein said light emitting diode is in series with a protective resistor.

* * * * *